United States Patent [19]

Parker

[11] Patent Number: 5,553,613
[45] Date of Patent: Sep. 10, 1996

[54] NON INVASIVE BLOOD ANALYTE SENSOR

[75] Inventor: Dawood Parker, Whitland, Wales

[73] Assignee: Pfizer Inc., New York, N.Y.

[21] Appl. No.: 291,632

[22] Filed: Aug. 17, 1994

[51] Int. Cl.$^6$ .................................................. A61B 5/00
[52] U.S. Cl. ............................................................ 128/633
[58] Field of Search ........................................ 128/633, 664

[56] References Cited

U.S. PATENT DOCUMENTS

| | | | |
|---|---|---|---|
| 4,014,321 | 3/1977 | March . | |
| 4,655,225 | 4/1987 | Dähne et al. | 128/633 |
| 4,971,062 | 11/1990 | Hasebe et al. | 128/664 |
| 5,054,487 | 10/1991 | Clarke . | |
| 5,137,023 | 8/1992 | Mendelson et al. | 128/633 |
| 5,279,295 | 1/1994 | Martens et al. | 128/633 |
| 5,297,554 | 3/1994 | Glynn et al. | 128/633 |
| 5,313,941 | 5/1994 | Braig et al. | 128/633 |
| 5,321,265 | 6/1994 | Block . | |
| 5,337,745 | 8/1994 | Benaron | 128/633 |

FOREIGN PATENT DOCUMENTS

| | | | |
|---|---|---|---|
| 9203965 | 3/1992 | WIPO | 128/633 |
| 9217765 | 10/1992 | WIPO . | |
| 9307801 | 4/1993 | WIPO . | |
| 9316629 | 9/1993 | WIPO . | |

OTHER PUBLICATIONS

Sodickson and Block, "Kromoscopic Analysis", Clinical Chemistry, vol. 40, No. 9, 1994, pp. 1838–1844.

Primary Examiner—Angela D. Sykes
Assistant Examiner—Eric F. Winakur
Attorney, Agent, or Firm—Peter C. Richardson; Lawrence C. Akers; Mark Dryer

[57] ABSTRACT

A device for the non-invasive measurement of the concentration of a specific analyte, particularly glucose, in arterial blood flowing in a patient's body part, which device comprises a solid first portion having a surface profile adapted to be held against the selected body part, a source of near infrared radiation mounted in a second portion associated with said first portion such that near infrared radiation is transmitted through or reflected from said body part, a third portion containing a detector and filters to receive radiation transmitted through or reflected from said body part, to select signals generated by the pulsatile component of the absorption spectrum and to provide a ratio representative of the desired concentration. A method for the determination of glucose concentration in arterial blood is also disclosed.

10 Claims, 5 Drawing Sheets

NON INVASIVE BLOOD ANALYTE SENSOR

FIELD OF THE INVENTION

This invention relates to a device for the non-invasive measurement of the concentration of a specific analyte in arterial blood. More particularly, the invention is concerned with the measurement of the concentration of glucose in arterial blood. The invention is also concerned with a method for measuring the concentration of an analyte, particularly glucose, in arterial blood.

BACKGROUND OF THE INVENTION

Many techniques for determining the presence of and measuring the concentration of various analytes in human blood are known in the art. These include invasive procedures involving the extraction of samples with needles or syringes and examination in an extra-corporeal analyser or the insertion in a blood vessel of a catheterized sensor and the measurement of blood parameters in vivo.

The development of non-invasive blood monitors or sensors is comparatively new, particularly for the determination of glucose concentration.

Although blood glucose levels in people without diabetes vary very little, usually staying within the range of about 4 to 7 mmol./L.; in people who have diabetes blood glucose levels vary considerably, even after treatment with insulin. The variation of glucose levels in diabetes tends to follow a fairly predictable pattern.

Medical evidence shows that the control of blood sugar, primarily glucose, levels in diabetics reduces the risk of the complications often resulting from diabetes. Accordingly, many samples may be taken for analysis during the course of a single day. The analysis is used to determine whether insulin or extra food or a glucose tablet is required to adjust an abnormal high or low glucose concentration.

The self-monitoring of blood glucose by the patient is considered by many clinicians to be the most important advance in the treatment of diabetes since the discovery of insulin. Because many patients consider the finger-lancing necessary for self-monitoring to be painful, inconvenient and embarrassing, and moreover, self-monitoring tends to be expensive, a less invasive method is clearly desirable.

U.S. Pat. Nos. 5,028,787 and 5,086,229 disclose an instrument and method for measuring blood glucose using near infrared energy introduced into a vein or artery of a subject, detecting the emerging signal in a detector which provides an electrical signal and processing the signal to provide a read-out indicative of the glucose concentration.

U.S. Pat. No. 5,070,874 discloses a method and apparatus for non-invasive determination of the concentration of glucose in a patient which uses near infrared radiation over a narrow range of wavelengths about 1660 nanometers (nm), derives a first and second expression as functions of the wavelength and determines the glucose concentration by calculations from said expressions.

Biological tissue is relatively transparent to near infrared (NIR) radiation having a wavelength within the range of about 700 to 1100 nm. U.S. Pat. No. 5,070,874 also refers to "near infrared" radiation, but the method disclosed therein relates to radiation of a somewhat longer wavelength in the region of 1660 nm. Although there is no universal definition of the range of wavelengths for NIR and wavelengths from 600 to 2500 nm have been quoted; as used herein NIR radiation is defined as radiation having a wavelength within the aforesaid range of about 700 to 1100 nm. Thus, the radiation used in the device and method of the present invention is clearly distinct from that used in the method of U.S. Pat. No. 5,070,874, and the significance of this distinction will be apparent from the description hereinafter.

The technique underlying the present invention is predicated upon the transparency of biological tissue to NIR radiation and is designated herein as pulse NIR spectroscopy. In this technique the NIR radiation transmitted through or reflected from biological tissue, for example, tissue located in a finger or ear-lobe, is filtered and detected. The radiation detected consists of a pulsatile component and a constant component. The constant component results from the absorption of radiation by skin, bone, tissue, venous and mixed venous blood, which are all constant light absorbers. The varying, pulsatile component results uniquely from the pulsating arterial blood in the path of the radiation. The magnitude of the pulsatile component at a glucose-sensitive wavelength is related to the glucose concentration in arterial blood. By using a technique involving the pulsatile component only, the influence of the constant or static absorbers is eliminated.

Although the procedure disclosed in U.S. Pat. Nos. 5,028,787 and 5,086,229 uses near infrared energy, the disclosure does not differentiate between the various tissue components, for example, venous and arterial blood, and there is no disclosure or suggestion of detecting and measuring the pulsatile component only. It has now been found that by taking measurements on the pulsatile component only the complex and expensive instrumentation required for prior art procedures may be eliminated and a low-cost device providing accurate non-invasive measurement of a desired analyte, particularly glucose, in arterial blood may be made. The measurements are made at a glucose-sensitive wavelength and at a reference wavelength. A relationship is then established between the ratio (R) of these two measurements and the blood glucose concentration determined from drawn blood samples. This relationship is incorporated in the monitoring device and forms the basis for subsequent non-invasive glucose concentration measurement.

SUMMARY OF THE INVENTION

In accordance with the present invention there is provided a device for the non-invasive measurement of the concentration of a specific analyte in arterial blood flowing in a patient's body part, which device comprises a solid first portion having a surface profile adapted to be held against the selected body part, a source of near infrared radiation mounted in a second portion associated with said first portion such that near infrared radiation is transmitted through or reflected from said body part and provides an absorption spectrum of said arterial blood, a third portion containing detection means located to receive radiation transmitted through or reflected from said body part, which detection means comprises at least two filters, including a first filter selective for a radiation signal having a first wavelength identifiable with the specific analyte and a second filter selective for a radiation signal having a second wavelength corresponding to a reference signal, said signals being generated by a pulsatile component of the absorption spectrum only, and a detector adapted to receive and process said signals to provide a ratio representative of the desired concentration.

A particularly preferred embodiment of the device according to the invention is a device which is adapted to measure the concentration of glucose in arterial blood and in this preferred device the first wavelength is at an isobestic point within the range of about 1000 to 1110 nm. Also, the preferred embodiment is a device adapted to take measurements from a finger.

The invention also provides a method for measuring the concentration of a specific analyte, particularly glucose, in arterial blood flowing in a patient's body part, for example, a finger, which comprises placing said body part against a device comprising a source of near infrared radiation and detection means comprising at least two filters and a detector, irradiating said body part with radiation from said source to obtain a near infrared absorption spectrum of the arterial blood, filtering out of said spectrum a first wavelength signal identifiable with the specific analyte and a second wavelength signal corresponding to a reference signal and using the detector to process said signals and provide a ratio representative of the concentration of the analyte.

When the specific analyte is glucose, the first wavelength is preferably at an isobestic point within the range of about 1000 to 1110 nm.

BRIEF DESCRIPTION OF THE DRAWINGS

The invention will now be particularly described with reference to the accompanying drawings, in which.

DETAILED DESCRIPTION OF THE INVENTION

Figure 1:
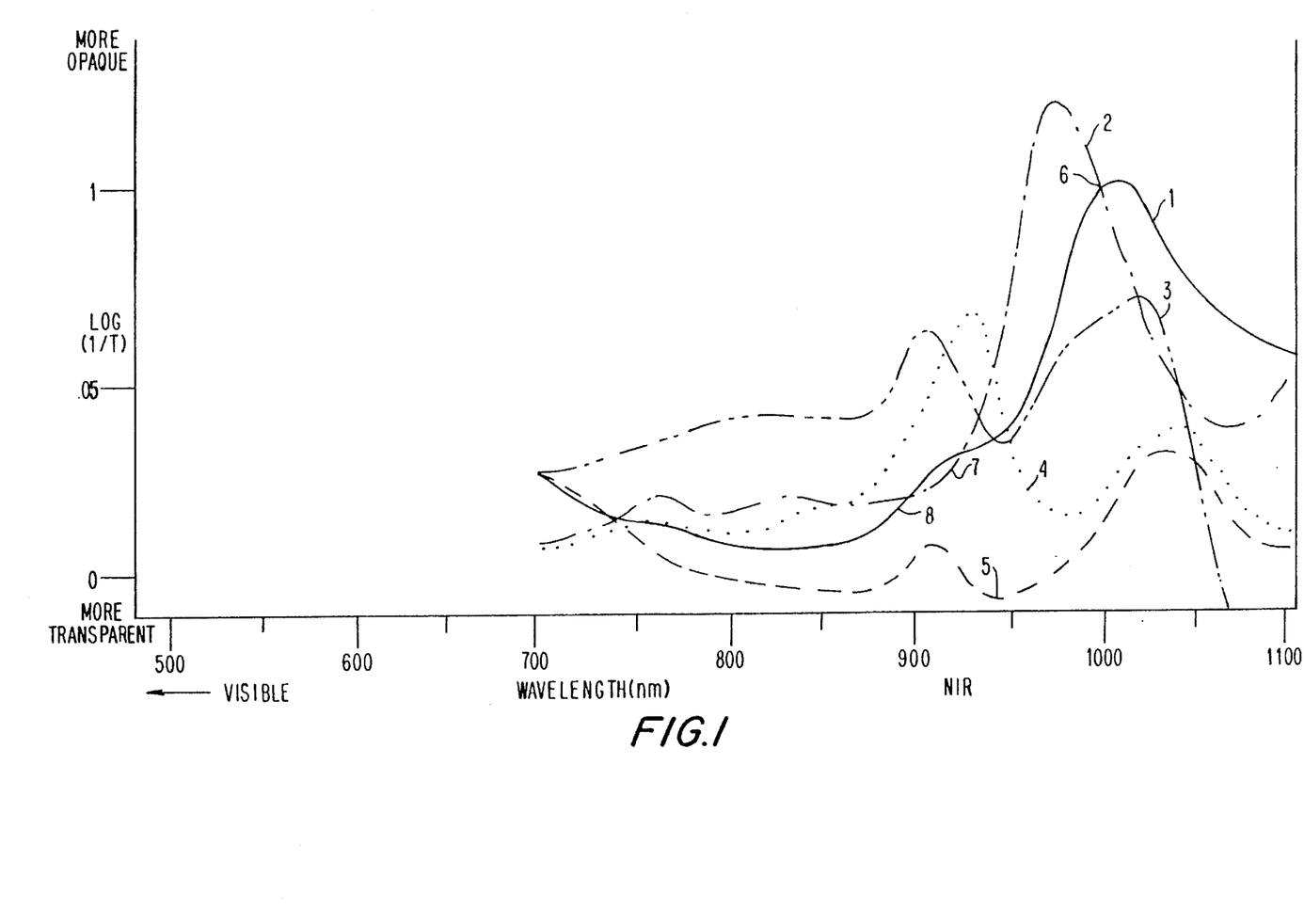
FIG. 1 illustrates the absorbance spectra of blood constituents.

NIR radiation is absorbed by living tissue because the biological material in the tissue contains —OH, —NH and —CH molecular bonds and these bonds interact with NIR radiation. As a result, the biological materials exhibit distinct absorbance spectra and the spectra of several major components in blood for NIR radiation within the range of 700–1100 nm are illustrated in FIG. 1 of the accompanying drawings. In FIG. 1 the spectral lines for the blood components are designated as follows: 1 is glucose; 2 is water; 3 is collagen; 4 is fat; and 5 is albumin.

The isobestic points, i.e., the points where the spectral lines cross, of glucose and water are located at 1000 nm (point 6), 920 nm (point 7) and 900 nm (point 8). The peak absorbance wavelength for glucose is at about 1034 nm and the peak absorbance wavelength for water is at about 970 nm.

Biological material is highly transparent to NIR so the absorption in this wavelength range is very low. Furthermore, the absorption spectra interfere with each other, i.e., the spectral lines overlap, as illustrated in FIG. 1. These factors make quantitative measurements difficult and, in the past, have resulted in the neglect of analysis of biological material by NIR. The situation has changed in recent times mainly as the result of progress in instrumentation and data analysis techniques, so that it is now possible to obtain considerable information from complex NIR spectra. However, prior to the present invention, this has been achieved by the development of expensive scanning techniques combined with complex statistical data analysis resulting in costly equipment.

It has now been found that the measurement technique may be simplified and the need for scanning optical instrumentation and complex data manipulation avoided by using the pulsatile nature of arterial blood only. This approach makes possible the development of a low-cost, home monitoring device for blood analytes, particularly glucose. The approach is also applicable for the measurement of other analytes such as cholesterol.

The technique utilized in the present invention is pulse NIR spectroscopy, which approach was developed from three significant observations, as follows:

1. Glucose in blood can be detected at a peak absorption wavelength of 1034 nm;

2. A reasonable wavelength against which to reference the glucose (or other analyte, for example, cholesterol) measurement, is 970 nm, being the absorption peak for water; and 3. The pulsatile part of the transmitted NIR signal is due to arterial blood only. By confining measurements to the pulsatile part of the transmitted signal it is possible to uniquely identify constituents of arterial blood. The influence of all constant optical absorbers such as skin, bone, tissue and venous blood (i.e., non-pulsing absorbers) is thus automatically eliminated. This greatly simplifies the measurement technique.

Figure 2:
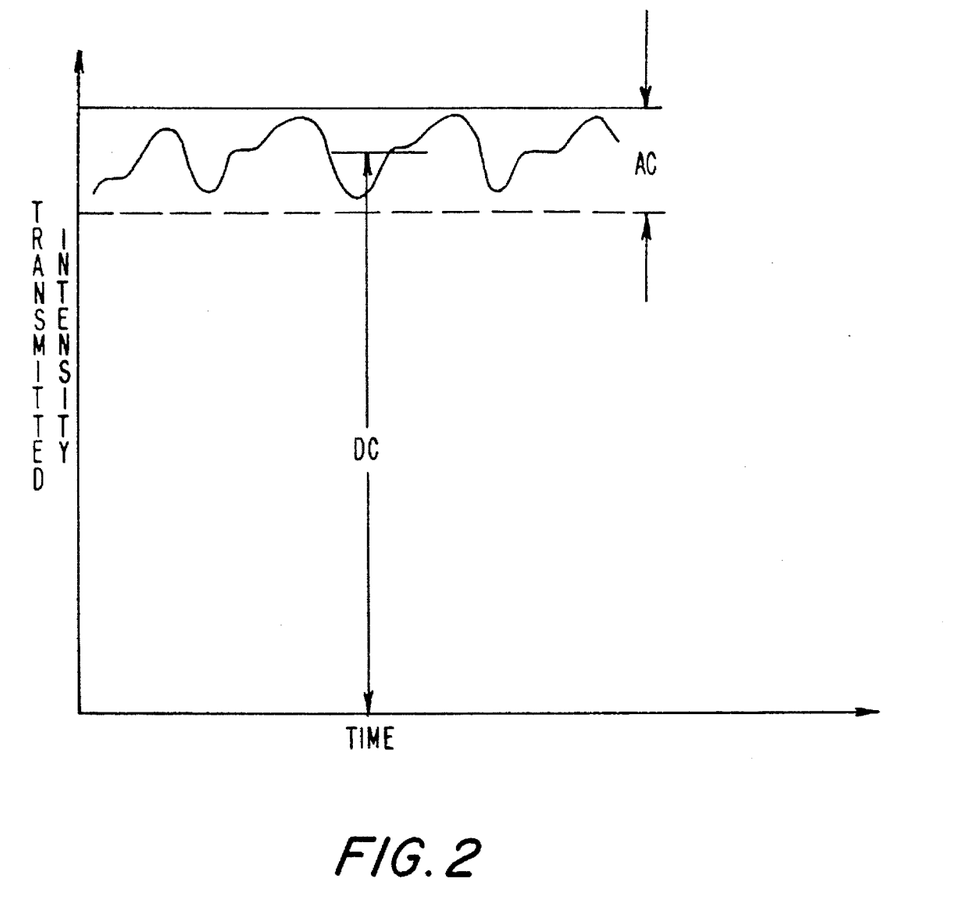
FIG. 2 illustrates a characteristic wave form for radiation transmitted through living tissue from a constant-intensity radiation source.

The significance of observation 3 is illustrated in FIG. 2 of the accompanying drawings. NIR radiation transmitted through living tissue, for example, a finger, is filtered and detected. The radiation reaching the photodetector at a selected wavelength (as determined by the filter) has a characteristic wave form as shown in FIG. 2. The detected signal consists of a constant component and a pulsatile component. It is convenient to define the constant or static component as the direct current (DC) signal and the pulsatile component as the alternating current (AC) signal.

The amplitude of the DC signal is dependent upon the intensity of the light source, the sensitivity of the detector and the concentration of absorbers that are present. The amplitude of the AC signal is dependent upon the same factors as well as the volume of blood change per pulse. To obtain a useful comparison between two or more wavelengths, the AC signals must be scaled by the DC signals. Dividing the AC level by the DC level, at each wavelength, gives a corrected or scaled AC level which is no longer a function of the incident intensity.

According to the present invention the amplitudes of both the AC signal and the DC signal are calculated within a period of N pulses. Assuming within this period M samples are taken at each wavelength the amplitude of the DC signal at each wavelength is obtained from the mean value of the NxM samples. The amplitude of the AC signal is obtained from the mean value of the absolute variation relative to the mean value of the stated NxM samples. The advantage of this method for calculating the amplitude of the AC signal is that the AC value is less sensitive to interference such as that due to movement than conventional methods such as taking the pulse peak-to-peak value.

The scaled or normalized AC signals (AC/DC) at different wavelengths are then linearly transformed in the calibration algorithm. Since the wavelengths chosen are sensitive to the relevant blood constituents, the corresponding AC/DC at these wavelengths (narrow bands) provides information of the nature of the analytes. By following conventional spectroscopic techniques the concentration of the analytes may be represented by the linear combination of the optical densities (O.D.) at these wavelengths. The optical density is a linear transformation of the AC/DC signal.

Figure 3:
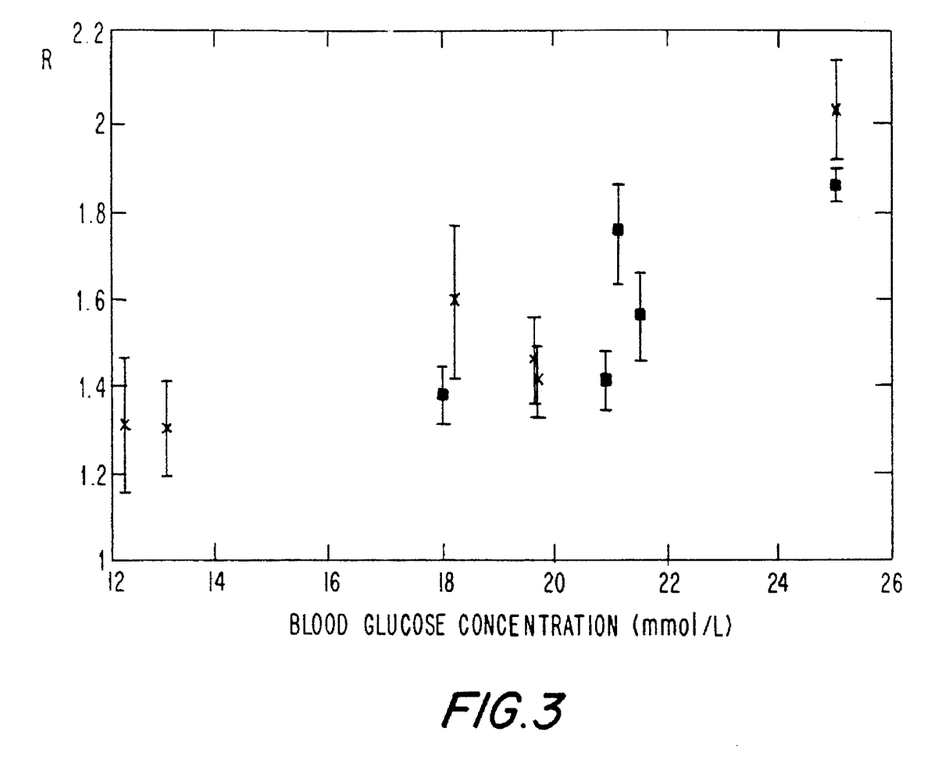
FIG. 3 is a plot of the ratio between normalized transmission signals at two wavelengths and the glucose concentration obtained by analyzing blood samples with a commercial self-monitoring device.

To illustrate the effect of the above procedure, a comparison of the NIR measurement represented by the ratio R between the normalized AC signals at 1000 nm and 970 nm and the glucose reading obtained with a commercial blood glucose meter for a diabetic volunteer was made. The results are illustrated in FIG. 3 of the accompanying drawings. In FIG. 3 the solid boxes are data points from the first experiment (normalized AC signals) and the crosses are data points from the second experiment (glucose reading with commercial instrument).

Figure 4:
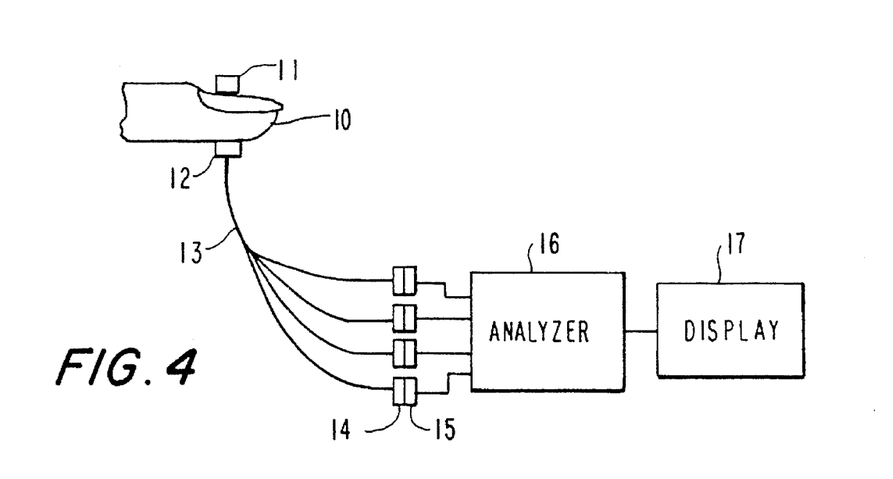
FIG. 4 is a schematic representation of one embodiment of the invention using transmitted NIR radiation through a finger.

A schematic representation of an embodiment of the device according to the invention is illustrated in FIG. 4 of the accompanying drawings. The device is adapted to obtain measurements from radiation transmitted through a finger 10. A source of radiation 11 is placed in contact with the top of the finger. A preferred source is a low-cost, self-focused, white-light source, for example, a low-cost krypton bulb. The white-light radiation includes NIR radiation in the range 600–1300 nm. The wide band of white light optical radiation illuminates the finger in which arterial blood vessels are located. On the lower side of the finger, diametrically opposite the white-light source, is placed one end of a detection means comprising a radiation collector 12, usually a focusing lens, to which is attached a bundle of optical fibers 13. In the embodiment illustrated in FIG. 4, the bundle contains four fibers. The radiation transmitted through the finger passes into the fiber bundle wherein it is distributed into four equal parts. The end of each fiber distal from the collector is connected to a band-pass filter 14 selective to a specific wavelength of interest. Each of the filters is connected to a photodetector 15 which converts the transmitted radiation at the specific wavelength into an electrical signal. Each of the signals from the photodetectors is processed in an analyzer 16 which analyzes the data contained in the signal and translates it into visual form which is shown in a display 17. The data contained in each signal gives information at the particular wavelength about the interaction between the radiation and the arterial blood constituents of interest and also includes interfering information from the interaction between the radiation and other biological components such as bones and soft tissue, as well as interference arising from physical movement of the finger. With appropriate signal processing the useful information is retained and the interfering information is suppressed. The enhanced signal is then used to derive the concentration of the analyte, for example glucose, in the arterial blood.

A sophisticated version of the device schematically illustrated in FIG. 4 is shown in FIGS. 5–9. This device is intended for home use and is intended to be conveniently carried in a handbag or pocket.

Figure 5:
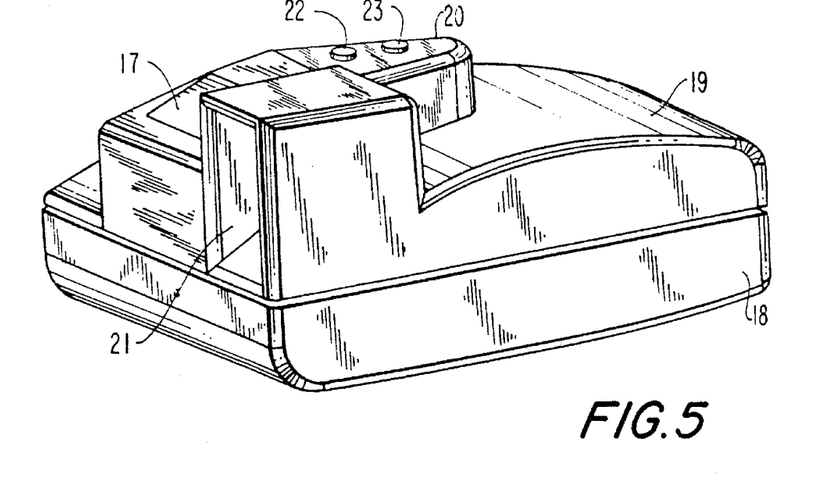
FIG. 5 is a perspective view of a proposed hand-held device incorporating the features of the invention.
Figure 6:
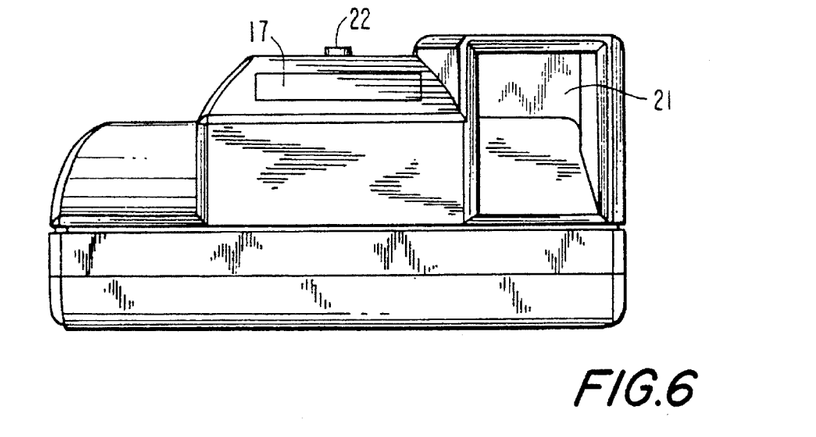
FIG. 6 is an end elevation of the device of FIG. 5.
Figure 7:
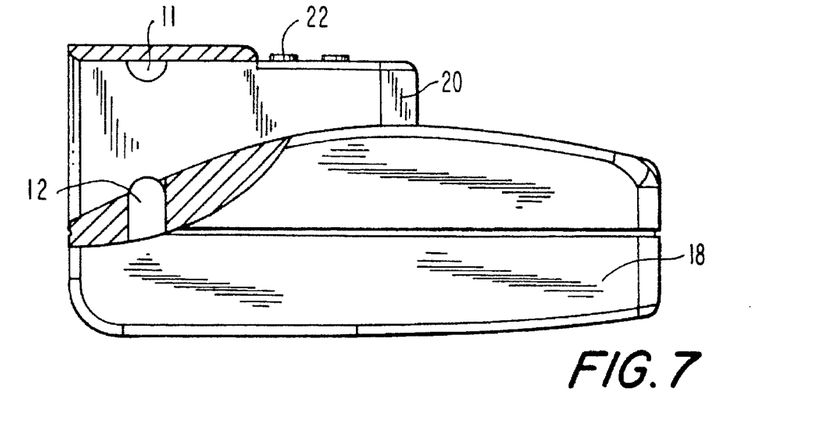
FIG. 7 is a side elevation, partly in section, of the left side of the device of FIG. 5.
Figure 8:
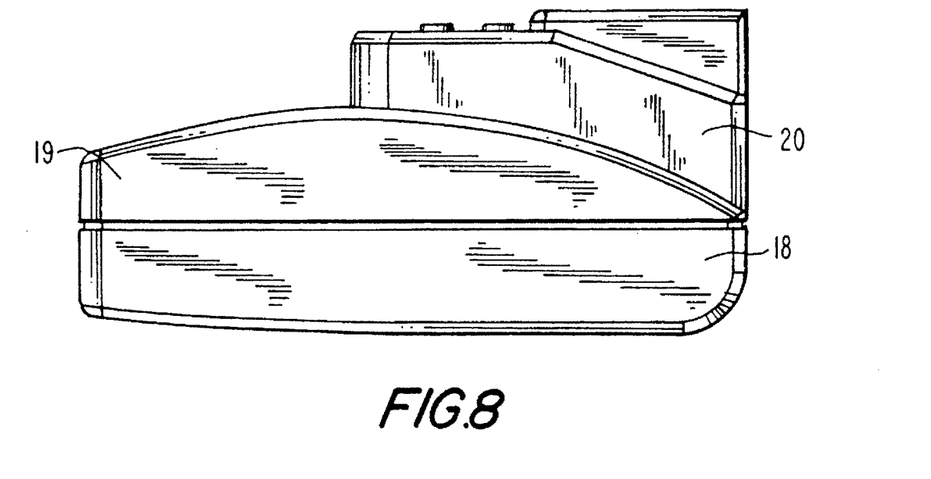
FIG. 8 is a side elevation of the right side of the device of FIG. 5.
Figure 9:
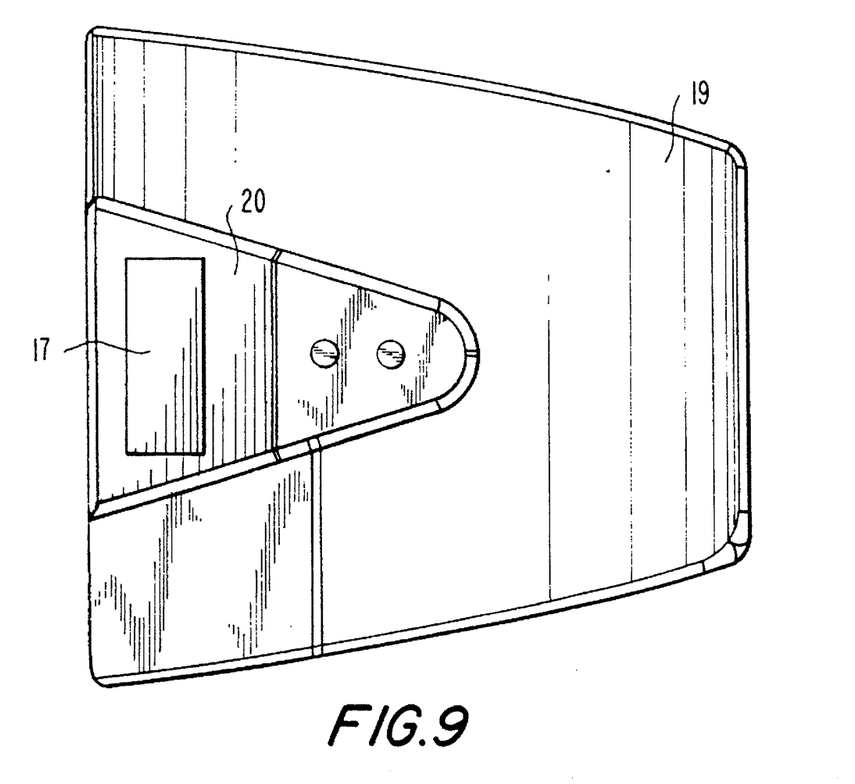
FIG. 9 is a plan view of the device of FIG. 5 viewed from above.

The device illustrated in FIG. 5 consists of an integral body comprising a base portion 18 which houses the detection means, including filters, photodetectors and analyzer, designated 14, 15 and 16 in the schematic version of FIG. 4, and the software associated therewith. The base also includes a compartment (not shown) for housing a battery to provide the electrical power source. If desired, the device also may include a power inlet point to accept power from a standard electrical outlet in the home. The upper portion 19 of the device is shaped to accept a patient's hand when placed flat against the upper surface thereof and includes a substantially triangular shaped raised portion or deck 20. The configuration of the upper portion is such that when the palm of the right hand is placed on the surface thereof the index finger lies to the left of the deck forming a "V" with the other three fingers which lie to the right of the deck. It is intended that the device be made in a number of standard sizes to accommodate hands and fingers of different sizes. Also a left hand version may be provided if desire by the patient.

When the hand is placed on the surface of the device so that the fingers form a "V" around the deck 20, the index finger enters into and is held by a tunnel 21 on the left hand side of the deck. The source of radiation 11 is located in the roof of the tunnel and the collector 12 for the detection means is located on the floor of the tunnel. The shape and size of the tunnel is chosen so that the index finger of a particular patient may be held therein with as little movement as possible.

The surface of the deck contains one or more push button switches 22, 23 for performing desired functions such as switching the source of radiation on and off and, if desired, lighting up the display 17 and choosing different data to be displayed. The display panel 17 is preferably a digital display which gives a read-out corresponding to the concentration of the analyte of interest, for example, glucose.

To enable the device to be used for the measurement of the concentration of a desired analyte, glucose being chosen hereinafter as the preferred analyte of interest, the device is first calibrated. The arterial blood glucose concentration is determined from a number of blood samples and the device is calibrated by establishing a relationship between R (the ratio of selected amplitudes) at each wavelength and the previously determined blood glucose concentration. The relationship is then incorporated in the device and forms the basis of all subsequent non-invasive glucose concentration measurements for the particular patient.

Once an analyte-sensitive wavelength has been established, alternative parameters may be used to determine the ratio R. Because it exhibits a distinctive high absorption spectral line at NIR wavelengths, water may be conveniently chosen as a reference parameter. A first alternative for the determination of R is the ratio between the peak amplitude of absorption at the glucose-sensitive wavelength (1034 nm) and the water absorption peak at 970 nm.

A second alternative is to calculate R as the ratio between the areas under the curve for each spectral line. This second alternative probably gives a somewhat more accurate determination when there is difficulty in taking a reading at the exact peak of the absorption curve; for example due to the absence of a filter specific for the exact wavelength peak.

A third alternative, and the one particularly preferred for the device of the present invention, is to determine R as the ratio between absorption amplitudes at chosen isobestic points between the spectral lines for glucose and water. It will be noted from FIG. 1 that a convenient isobestic point 6 occurs at a wavelength of 1000 nm and two other (reference) isobestic points occur at 900 nm (8) and 920 nm (7). The latter points are in a wavelength range where the water absorption is very nearly constant.

Upon determination of the relationship between R and the blood glucose concentration, the relationship is incorporated in the device and forms the basis for all subsequent non-invasive glucose concentration measurements.

By identifying other wavelengths in the NIR which are sensitive to other analytes, (for example cholesterol), the same technique may be used for the non-invasive determination of the concentration of such other analytes.

Arterial blood pulses and is the only body material which exhibits a pulsatile component. Although the pulsatile component of the absorbance spectrum is less than 1% of the transmitted (or reflected) signal, it is nevertheless detectable and may be isolated in accordance with the technique of the present invention.

By applying the technique of the present invention to the pulsatile component of arterial blood only all non-pulsatile overlapping interferents are substantially eliminated. In the event that interferents in the arterial blood still affect the glucose measurement, the situation may be corrected as follows:

(a) If the interference is slow-changing, the effect may be neglected during a measurement of glucose lasting only a few seconds; or (b) Provision for extra measuring wavelengths may be made and a correcting algorithm developed to eliminate anomalies resulting from arterial blood interferents.

Particular advantages of the pulsatile technique utilized in the present invention include:

1. There are fewer interferents in arterial blood than in other body materials;
2. Fewer wavelengths are required for analysis;
3. Signal processing is simpler than in prior art techniques;
4. Low cost; and
5. There is less interference from water.

Measurements are made in the NIR region of the electromagnetic spectrum where biological tissue is relatively transparent and, consequently, the instrumentation, particularly the optical components, is inexpensive. Thus, because the tissue at the finger tip is relatively transparent a powerful radiation source is not necessary and the low-cost light source described hereinabove and the detector are quite inexpensive.

Furthermore the device may be made to operate in the transmission or reflectance mode. The device described herein operates in the preferred transmission mode.

The finger-positioned monitoring device described herein is adapted to measure through the same tissue volume on a day-to-day or hour-to-hour basis.

NIR measurement is sensitive to temperature changes and, accordingly, it is important that the temperature should be constant to obtain meaningful readings. Heating the finger to a standard monitoring temperature would consume too much power and render battery operation non-feasible. However, a correction factor for temperature changes may be incorporated in the software. This feature is known in the art and consumes no extra power.

In the operation of the device according to the invention it is recommended that the patient uses a contact gel between the tissue (finger), the light source and the detector. This achieves constant light coupling which improves reproducibility.

The device of the present invention preferably uses a low-cost white light source which is a focused Krypton flashlight bulb. This is a broad-based source, i.e., it contains many wavelengths.

The advantages of this light source are:

(a) low cost;
(b) any wavelength in the range of measurement is available;
(c) intensity of light at different chosen wavelengths is constant;
(d) constant intensity means lower cost electronics and no equalization of intensity is required in the circuitry; and
(e) very low power consumption and thus battery power is possible.

A device made in accordance with the present invention provides a low-cost glucose (or other analyte) monitor for home use. The incorporation of appropriate analytical software associated with appropriate switching should enable a low-cost multi-analyte monitor to be made.

I claim:

1. A device for non-invasive measurement of concentration of a specific analyte in arterial blood flowing in a patient's body part, which device comprises a first portion having a surface profile adapted to be held against said body part, a low-cost, self-focused, white light source of near infrared radiation mounted in a second portion associated with said first portion such that a wide band of white light optical radiation illuminates the body part and near infrared radiation is transmitted through or reflected from said body part to provide an absorption spectrum of said arterial blood, a third portion containing detection means located to receive radiation transmitted through or reflected from said body part, which detection means comprises a radiation collector to which is attached a bundle of optical fibers, each of which fibers has a distal end connected to one of at least two filters, including a first filter selective for a first radiation signal having a first wavelength identifiable with the specific analyte and a second filter selective for a second radiation signal having a second wavelength corresponding to a reference signal, said first and second signals being obtained from a pulsatile component of the absorption spectrum only, and a detector adapted to receive and process said first and second signals to provide a ratio representative of the desired concentration.

2. A device according to claim 1, in which the specific analyte is glucose and the first wavelength is at an isobestic point within the range of about 1000 to 1110 nm.

3. A device according to claim 1, in which the selected body part is a finger.

4. A device according to claim 3, in which said second portion and said first portion form an integral combination which defines a tunnel having a roof and a base adapted to accommodate the patient's finger with the source of radiation mounted in the roof of the tunnel and the third portion containing the detection means is part of the first portion defining the base of the tunnel whereby radiation is transmitted through the finger and received by said detection means.

5. A device according to claim 1 which includes display means for providing a visual representation of the concentration measurement.

6. A method for measuring the concentration of a specific analyte in arterial blood flowing in a patient's body part, which comprises placing said body part against a device comprising a low-cost, self-focused, white light source of near infrared radiation and detection means comprising a radiation collector to which is attached a bundle of optical fibers, each of which fibers has a distal end connected to one of at least two filters and a detector, irradiating said body part with a wide band of white light optical radiation from said source to obtain a near infrared absorption spectrum of a pulsatile component of the arterial blood, filtering out of the pulsatile component of said spectrum a first wavelength signal identifiable with the specific analyte and a second wavelength signal corresponding to a reference signal and using the detector to process said first wavelength and second wavelength signals and provide a ratio representative of the concentration of the analyte.

7. A method according to claim 6, in which the specific analyte is glucose and the first wavelength is at an isobestic point within the range of about 1000 to 1110 nm.

8. A method according to claim 6, in which the body part is a finger.

9. A method according to claim 8, in which the finger is held between the source of the near infrared radiation and the detection means and the desired measurement is obtained from the absorption spectrum resulting from transmission of radiation through the finger.

10. A method according to claim 9, in which a contact gel is spread on the finger to achieve constant light coupling and improve reproducibility.

\* \* \* \* \*